US007395710B2

(12) United States Patent
Daoud

(10) Patent No.: US 7,395,710 B2
(45) Date of Patent: Jul. 8, 2008

(54) SYSTEM AND METHOD FOR MONITORING A FILTER

(75) Inventor: Mohamed I. Daoud, Dunlap, IL (US)

(73) Assignee: Caterpillar Inc., Peoria, IL (US)

( * ) Notice: Subject to any disclaimer, the term of this patent is extended or adjusted under 35 U.S.C. 154(b) by 106 days.

(21) Appl. No.: 11/362,863

(22) Filed: Feb. 28, 2006

(65) Prior Publication Data

US 2007/0199380 A1 Aug. 30, 2007

(51) Int. Cl.
*G01N 29/04* (2006.01)

(52) U.S. Cl. .............................. 73/584; 73/596; 96/417

(58) Field of Classification Search .................. 73/584, 73/596, 599; 95/1; 96/417
See application file for complete search history.

(56) References Cited

U.S. PATENT DOCUMENTS 5,497,099 A 3/1996 Walton
6,328,647 B1 12/2001 Traudt
6,435,019 B1 8/2002 Vojtisek-Lom
6,666,070 B1 12/2003 Hagg et al.
6,964,694 B2 11/2005 Rauchfuss et al.
2004/0031386 A1* 2/2004 Rauchfuss et al. ............... 95/1
2005/0247131 A1 11/2005 Breuer

FOREIGN PATENT DOCUMENTS

JP 7310525 11/1995
JP 8121150 5/1996
WO WO 2004/026434 A1 * 4/2004

OTHER PUBLICATIONS

Treuhaft, Martin B., "Ultrasonic Agglomeration of Airborne Dusts and Diesel Exhaust Particulate to Enhance Inertial Separation," Southwest Research Institute, San Antonio, Texas, undated, pp. 1-33.
Zhi et al., "Radio-Frequency (RF) Technology for Filter Microwave Regeneration System," SAE Technical Paper Series, Publication No. 2000-01-2845, Oct. 16-19, 2000, pp. 7.
Daoud et al., "A Doppler Sensor for High Spatial Resolution Measurements of Unsteady Surface Pressure," Measurement Science and Technology, Institute of Physics Publishing, 2003, pp. 13-23.
Soot in Oil Analyzer, The Sootspec, undated, pp. 13-23.

* cited by examiner

*Primary Examiner*—John E Chapman
(74) *Attorney, Agent, or Firm*—Finnegan, Henderson, Farabow, Garrett & Dunner

(57) ABSTRACT

A monitoring assembly for a filter may include a transmitter, arranged on a first side of the filter, configured to emit sound waves. The monitoring assembly may also include a first receiver, arranged on the first side of the filter, configured to receive the sound waves. The monitoring assembly may further include a second receiver, arranged on a second side of the filter, configured to receive the sound waves.

20 Claims, 4 Drawing Sheets

50
38
ECM
52
54
34
REGENERATION DEVICE
10
RECEIVER
36
TRANSMITTER
16
48
44
56
FILTER
30
32
14
50
26
REGENERATION DEVICE
28
34
RECEIVER
18 20 22 24
12
46

SYSTEM AND METHOD FOR MONITORING A FILTER

TECHNICAL FIELD

The present disclosure relates generally to filter monitoring, and more particularly to a system and method for monitoring the state of a particulate filter.

BACKGROUND

Engines, including diesel engines, gasoline engines, natural gas engines, and other engines known in the art, may exhaust a complex mixture of air pollutants. The air pollutants may be composed of gaseous and solid materials, including, for example, particulate matter. Particulate matter may include unburned carbon particles, such as soot. Particulate matter may be generated during operation of an engine, as fuel is supplied to the engine and is combusted in one or more combustion chambers within the engine. The engine may expel this particulate matter along with other engine exhaust from the one or more combustion chambers through an exhaust line. If this particulate matter is not filtered or otherwise removed from the engine exhaust, these particulates may be vented to the environment. Due to increased attention on the environment, exhaust emission standards have become more stringent. The amount of particulates emitted from an engine may be regulated depending on the type of engine, size of engine, and/or class of engine.

In order to remove particulate matter from engine exhaust, an exhaust filtration system may be disposed within the exhaust line. The exhaust filtration system may include a particulate filter or trap that may remove particulate matter from the engine exhaust. Particulate filters may typically include a wire mesh medium through which the engine exhaust is passed. The wire mesh medium may filter or trap particulate matter from the engine exhaust. Use of the particulate filter for extended periods of time may cause particulate matter to buildup in the wire mesh medium, thereby causing the functionality of the filter and engine performance to decrease. To avoid this decrease, a heating element may be used to increase the temperature of the trapped particulate matter above the combustion temperature of the trapped particulate matter, thereby burning away the trapped particulate matter and regenerating the filter system. Although regeneration may reduce the buildup of particulate matter in the filter, repeated regeneration of the filter may result in a buildup of ash in the components of the filter over time, or may cause damage to the filter, possibly resulting in a deterioration of filter performance.

At least one system has been developed for diesel particulate filter monitoring. For example, U.S. Pat. No. 6,964,694 to Rauchfuss et al. ("Rauchfuss") discloses incorporating one or more acoustic sensors into an exhaust system of an engine for detecting one or more frequencies passing through a filter. The one or more acoustic sensors may be fluidly or mechanically coupled to portions of the exhaust system to determine the frequency caused by the exhaust flow through the filter. The acoustic emissions from the filter may be compared to a known filter state to determine the present filter state. However, if the engine in Rauchfuss is not in operation, and no exhaust flow is being produced, then there are no frequencies or sounds for the one or more acoustic sensors to detect. When there are no frequencies or sounds to detect, the system in Rauchfuss cannot readily determine the state and/or loading of the filter.

The present invention is directed to overcoming one or more of the problems set forth above.

SUMMARY OF THE INVENTION

In one aspect, the present disclosure is directed to a monitoring assembly for a filter. The monitoring assembly may include a transmitter, arranged on a first side of the filter, configured to emit sound waves. The monitoring assembly may also include a first receiver, arranged on the first side of the filter, configured to receive the sound waves. The monitoring assembly may further include a second receiver, arranged on a second side of the filter, configured to receive the sound waves.

In another aspect, the present disclosure is directed to a method of monitoring a particulate filter. The method may include transmitting sound waves from a first side of the filter with a transmitter, receiving the sound waves on the first side of the filter with a first receiver, and receiving the sound waves on a second side of the filter with a second receiver. The method may also include determining at least one value indicative of a variation between the sound waves received on the first side and the sound waves received on the second side.

In yet another aspect, the present disclosure is directed to an engine assembly. The engine assembly may include an engine having an exhaust line, a particulate filter operatively coupled to the exhaust line, and an acoustic apparatus operatively coupled to at least one of the exhaust line and the particulate filter. The acoustic apparatus may include a transmitter, arranged on a first side of the filter, configured to emit sound waves. The acoustic apparatus may also include a first receiver, arranged on the first side of the filter, configured to receive the sound waves. The acoustic apparatus may further include a second receiver, arranged on a second side of the filter, configured to receive the sound waves.

DETAILED DESCRIPTION

Exemplary embodiments of the present disclosure are illustrated in the accompanying drawings. Wherever possible, the same reference numbers will be used throughout the drawings to refer to the same or like parts.

Figure 1:
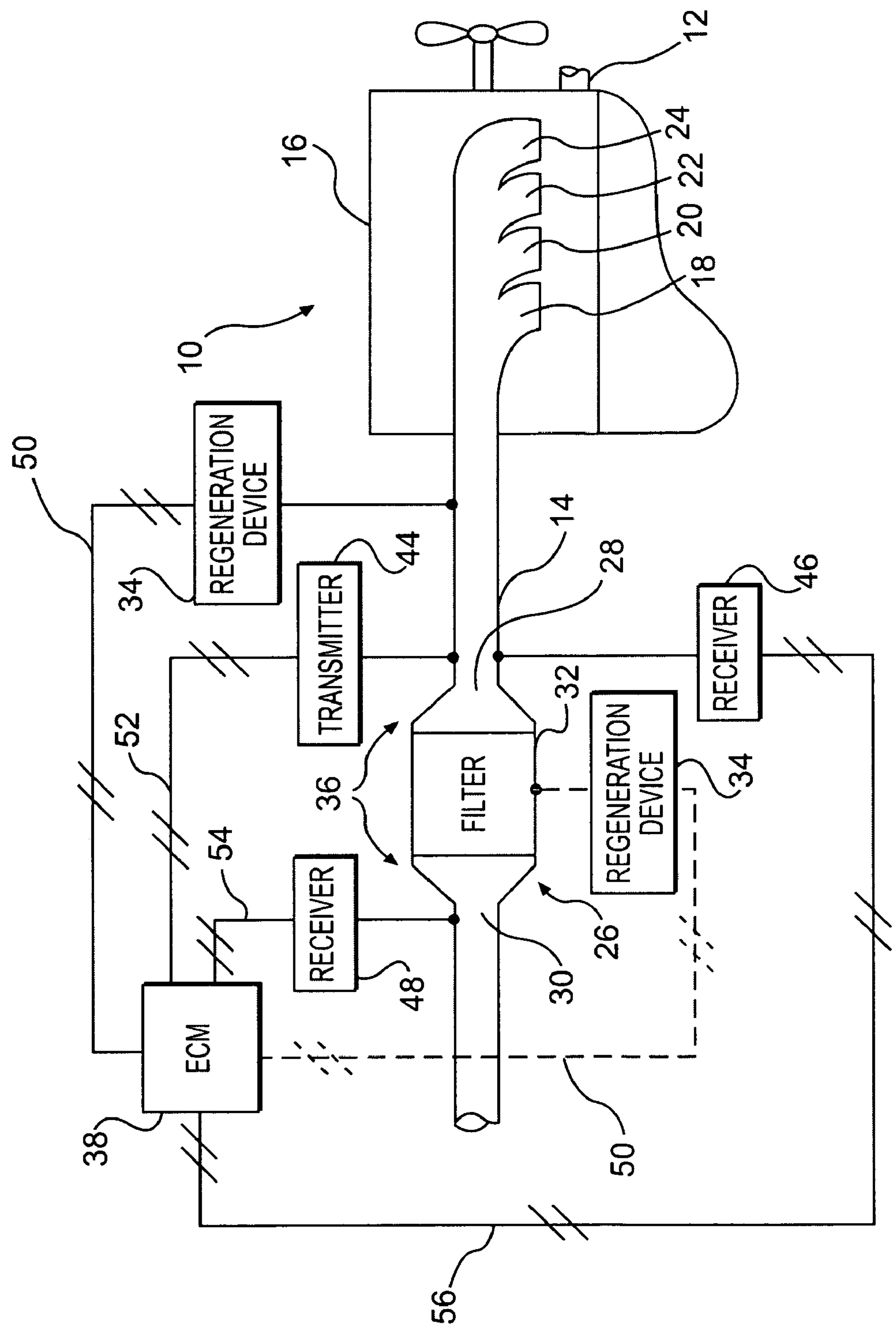
FIG. 1 is a diagrammatic illustration of an engine having a particulate filter assembly according to an exemplary embodiment of the present disclosure.

FIG. 1 illustrates a schematic representation of an internal combustion engine 10 including an intake line 12, an exhaust line 14, and an engine block 16. Intake line 12 may provide an intake path for air, recirculated exhaust gases, or a combination thereof. Gases from intake line 12 may be directed into one or more combustion chambers (not shown) housed in engine block 16. Exhaust line 14 may provide a path for exhaust gases to exit from the combustion chambers. An upstream portion of exhaust line 14 may split into one or more exhaust passages 18, 20, 22, and 24, each being operatively connected to one of the combustion chambers.

During operation of internal combustion engine 10, intake air may enter into the combustion chambers through intake line 12. The intake air and fuel may be combusted within the combustion chambers, and the exhaust generated by combustion may be evacuated from within the combustion chambers through exhaust passages 18, 20, 22, and 24. In one embodiment, exhaust line 14 may be coupled to four combustion chambers by four exhaust passages 18, 20, 22, and 24. However, any number of combustion chambers and exhaust passages may be used. Internal combustion engine 10 may include diesel engines, gasoline engines, natural gas engines, and other engines known in the art.

Figure 2:
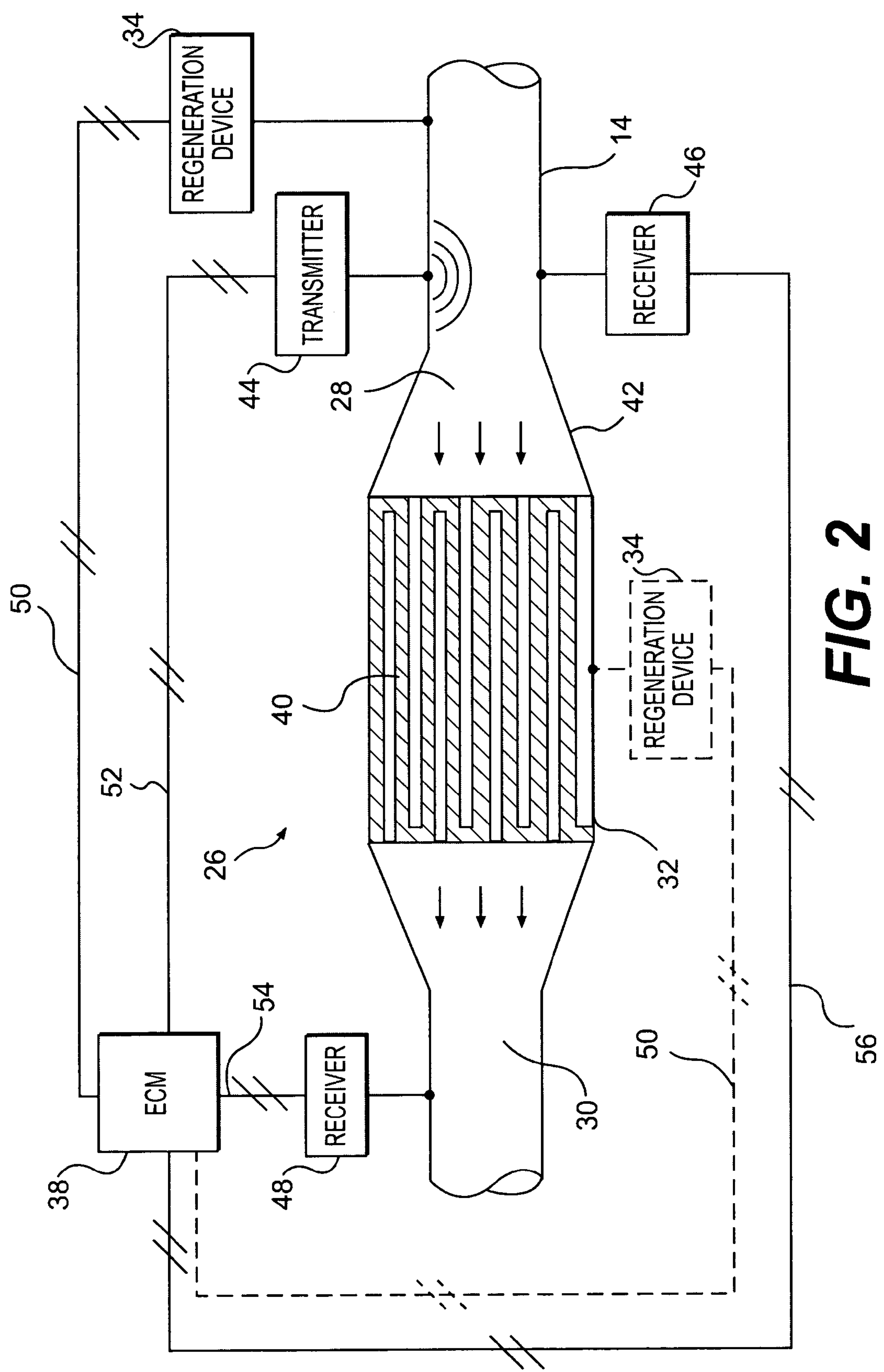
FIG. 2 is a diagrammatic illustration of the particulate filter assembly from FIG. 1.

Exhaust line 14 may be operatively connected to a particulate filter assembly 26. A stream of exhaust exiting from the combustion chambers through exhaust passages 18, 20, 22, and 24 may flow downstream through exhaust line 14 into particulate filter assembly 26. Particulate filter assembly 26 may be configured to filter or trap particulate matter in the exhaust stream as the exhaust stream passes therethrough. Particulate filter assembly 26 may include, for example, an inlet 28 for receiving the exhaust stream, an outlet 30 allowing filtered exhaust to exit from particulate filter assembly 26, a particulate filter 32 located between inlet 28 and outlet 30, a particulate filter regeneration device 34, an acoustic apparatus 36, and a controller, such as an electronic control module 38. Particulate filter assembly 26 is shown in greater detail in FIG. 2.

Particulate filter 32 may include any type of filter known in the art. In one embodiment, particulate filter 32 may include a filter element 40 located within a filter housing 42. Filter element 40 may be constructed of any material useful in removing pollutants and/or particulates from the exhaust stream, such as, for example, foam cordierite, sintered metal, ceramic, or silicon carbide. It is contemplated that filter element 40 may also include catalyst materials capable of collecting soot, NOx, sulfur compounds, particulate matter, and/or other pollutants known in the art. Such catalyst materials may include, for example, alumina, platinum, rhodium, barium, cerium, and/or alkali metals, alkaline-earth metals, rare-earth metals or combinations thereof. Filter element 40 may be situated horizontally, vertically, radially, or helically. Additionally or alternatively, filter element 40 may be arranged in a honeycomb, mesh, or any other suitable configuration so as to maximize the available surface area for filtration.

Particulate filter regeneration device 34 may be configured to increase the temperature of the exhaust stream produced by internal combustion engine 10 to a predetermined temperature. The predetermined temperature may include, for example, a regeneration temperature of particulate filter 32. In one embodiment, particulate filter regeneration device 34 may be operatively coupled to exhaust line 14 at a location upstream of particulate filter 32. It is also contemplated that particulate filter regeneration device 34 may be operatively coupled to filter housing 42 and/or filter element 40. Particulate filter regeneration device 34 may include, for example, a fuel injector and an igniter, heat coils, electrical conductors, and/or other heat sources known in the art. Such heat sources may be configured to assist in increasing the temperature of the exhaust stream through convection, combustion, and/or other methods of heat transfer. As the temperature of the exhaust stream increases, the temperature of the trapped particulate matter in particulate filter 32 may also increase. When the trapped particulate matter reaches the predetermined temperature, it may bum away, and thus, particulate filter 32 may be regenerated.

Acoustic apparatus 36 may include, for example, a transmitter 44 and one or more receivers 46 and 48. Transmitter 44 may be positioned at a location upstream of particulate filter 32, and may be configured to send sound waves towards and/or through particulate filter 32. It is contemplated that the sound waves transmitted by transmitter 44 may include ultrasounds and/or any other high or low frequency sonic emissions. In order to produce these emissions, transmitter 44 may include a transducer for converting electrical signals into sound waves. It is also contemplated that receivers 46 and 48 may also include transducers that may be similar or identical to the transducer of transmitter 44. The transducers of receiver 46 and 48 may be configured receive sound waves from transmitter 44, and may convert those sound waves into electrical signals. The transducers may include piezoelectric transducers, or any other suitable transducers known in the art capable of converting electrical signals/pulses to mechanical vibrations, and vice versa. The type of transducer chosen may depend on a host of factors, including, for example, its working frequency, size and weight, cost, corrosion resistance, and ability to withstand high temperature environments.

The transducers may be either permanently or removably coupled to exhaust line 14 or particulate filter 32 by one or more attachment devices (not shown), such as, for example, brackets, clips, welds, adhesives, and/or any other suitable attachment devices known in the art. In one embodiment, at least one of the transducers may be indirectly coupled so that a space may exist between the at least one transducer and exhaust line 14 or particulate filter 32. In another embodiment, at least one of the transducers may be directly mounted onto a surface of exhaust line 14 or particulate filter 32. In yet another embodiment, at least one of the transducers may be mounted so as to extend into exhaust line 14 or particulate filter 32.

Receiver 46 may be located on the same side of particulate filter 32 as transmitter 44, and thus, may receive sound waves directly from transmitter 44. Receiver 48 may be located on a side of particulate filter 32 opposite that of transmitter 44. By positioning receiver 48 on the opposite side, receiver 48 may receive sound waves from transmitter 44 after they have passed through particulate filter 32. By comparing the properties of the sound waves received by receiver 46 to the sound waves received by receiver 48, the type, kind, and/or magnitude of variation between the sound waves received by receivers 46 and 48 may be determined. The variation may be influenced by the physical properties of particulate filter 32, including, for example, the type of material used to make particulate filter 32, the shape and size of particulate filter 32, and/or the amount of particulate matter trapped in particulate filter 32. It is also contemplated that the variation may be indicative of damage to particulate filter 32, including, for example, melting and/or cracking. This process of analyzing the sound waves will be explained in further detail below.

In one embodiment of the present disclosure, acoustic apparatus 36 may be integrated and/or permanently coupled to exhaust line 14 and/or particulate filter assembly 26. Additionally or alternatively, acoustic apparatus 36 may include a portable diagnostic tool selectively coupled to exhaust line 14 and/or particulate filter assembly 26. In either case, acoustic apparatus 36 may be located proximate exhaust line 14 and/or particulate filter assembly 26, and thus, may be exposed to heat. Accordingly, acoustic apparatus 36 may include insulation (not shown) and/or a cooling system (not shown) to protect its components from being damaged by the heat.

Electronic control module 38 may include an electronic controller in the form of one or more microprocessors and one or more memory components. The microprocessors and memory components may include software code instruction sets that may be executed to perform various control and information functions, such as, for example, assisting in the operation of internal combustion engine 10, acoustic apparatus 36, and/or particulate filter regeneration device 34.

In one embodiment, electronic control module 38 may be configured to supply electrical signals/pulses to transmitter 44, and receive electrical signals/pulses from receivers 46 and 48 through electrical connections 52, 54, and 56. The transducer of transmitter 44 may convert the electrical signals/pulses into sound waves, such as, for example, ultrasounds. The type and kind of sound waves transmitted by transmitter 44 may be selectively adjusted by electronic control module 38 in terms of its frequency, intensity, wavelength, amplitude, and other properties, based upon the characteristics of internal combustion engine 10, particulate filter 32, particulate matter, and/or the working environment.

Receivers 46 and 48 may be configured to receive sound waves from transmitter 44. The transducers of receivers 46 and 48 may convert those sound waves into electrical signals/pulses that may be sent back to electronic control module 38 for recording and/or analysis. The electrical signals/pulses sent by receivers 46 and 48 may contain information indicative of the sound spectrum and characteristics of the sound waves received by receivers 46 and 48. It is also contemplated that receivers 46 and 48 may be configured to focus on one or more specific sound wave characteristics, such as, for example, frequency, intensity, wavelength, amplitude, and/or loudness. As such, receivers 46 and 48 may filter out extraneous data before sending electrical signals/pulses to electronic control module 38. Additionally or alternatively, electronic control module 38 may be configured to filter out extraneous data after receiving electrical signals/pulses from receivers 46 and 48.

Electronic control module 38 may operate transmitter 44 and receivers 46 and 48 continuously during operation of internal combustion engine 10 to constantly monitor the state of particulate filter 32. Additionally or alternatively, electronic control module 38 may operate transmitter 44 and receivers 46 and 48 intermittently. For example, in one embodiment, electronic control module 38 may not monitor particulate filter 32 during the initial operation of internal combustion engine 10. In such a state, electronic control module 38 may not supply electric signals/pulses to transmitter 44 or receive electronic signals/pulses from receivers 46 and 48, effectively turning acoustic apparatus 36 off. One or more sensors may be operatively connected to electronic control module 38 to supply electronic control module 38 with sensed values from internal combustion engine 10, particulate filter assembly 26, and/or exhaust line 14. If the sensed values fall outside of a predetermined range, electronic control module 38 may recognize the out-of-range condition as being related to loading of and/or damage to particulate filter 32. As such, electronic control module 38 may turn on acoustic apparatus 36 by sending electronic signals/pulses to transmitter 44, and receiving electronic signals/pulses from receivers 46 and 48.

It is also contemplated that electronic control module 38 may reverse the relationship between the various transducers. For example, in one mode of operation, the transducer of transmitter 44 may transmit sound waves, while transducers of receivers 46 and 48 may receive sound waves. However, by switching the direction of the electronic signals/pulses, one or both of the transducers of receivers 46 and 48 may be converted into transmitters (effectively converting one or both of receivers 46 and 48 into transmitters), while the transducer of transmitter 44 may be converted into a receiver (effectively converting transmitter 44 into a receiver).

During servicing, where internal combustion engine 10 may not be running and/or electronic control module 38 may not receive power, a service technician may attach a portable version of acoustic apparatus 36 on or near particulate filter assembly 26. The service technician may connect acoustic apparatus 36 to an external power source (not shown) to turn on transmitter 44 and receivers 46 and 48 to monitor particulate filter 32 and determine whether particulate filter 32 should be cleaned, repaired, or replaced. The external power source may include one or more batteries, a power outlet, and/or any other suitable power supply device. Thus, acoustic apparatus 36 may operate without having to run internal combustion engine 10.

When transmitter 44 and receivers 46 and 48 are turned on, sound waves may propagate from transmitter 44 towards receivers 46 and 48. The specific sound spectrum patterns and characteristics of the sound waves received by receiver 46 (upstream sound waves) may be recorded and analyzed by electronic control module 38. Similarly, the specific sound spectrum patterns and characteristics of the sound waves received by receiver 48 (downstream sound waves) may also be recorded and analyzed by electronic control module 38. Using its microprocessors and memory components, electronic control module 38 may conduct an analysis of the sound spectrum patterns and characteristics of the upstream and downstream sound waves. For example, electronic control module 38 may perform an analysis in the time and frequency domains of the upstream and downstream sound waves.

During the analysis, values, charts, and/or graphs representing the sound spectrum pattern and characteristics of the upstream and downstream sound waves may be determined. The values, charts, and/or graphs for the upstream and downstream sound waves may be compared and contrasted to detect any variations between the wave characteristics of the upstream and downstream sound waves.

In one embodiment, levels of variation may correspond to the load level (amount of particulate matter) in particulate filter 32. For example, if receivers 46 and 48 detect a low level of variation between the upstream and downstream sound waves, electronic control module 38 may interpret the low level as indicating that particulate filter 32 is relatively clean. If the level of variation is lower than it should be for a clean particulate filter, electronic control module 38 may interpret the lower level as indicating that particulate filter 32 is damaged. For example, electronic control module 38 may recognize, based on the lower level of variation, that a gap that may be allowing unaffected sound waves to pass through particulate filter 32. On the other hand, a higher level of variation may indicate that particulate filter 32 is loaded, or has become clogged.

Figure 3A:
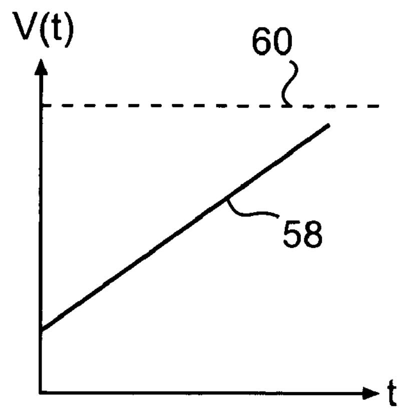
FIGS. 3A-3C are graphs illustrating exemplary trend curves related to the particulate filter assembly.

It is also contemplated that the level of variation of the sound waves may be plotted over time to form one or more trend curves, such as, for example, trend curves 58, 62, and 66. Trend curves 58, 62, and 66 may be analyzed by electronic control module 38, and/or may be displayed to a user or service technician on a visual display assembly (not shown), such as, for example, a computer screen, video monitor, or any other suitable device. In FIG. 3A, trend curve 58 may be representative of the level of variation between the upstream and downstream sound waves over time during the operation of internal combustion engine 10. The increase in the level of variation over time in trend curve 58 may indicate that particulate filter 32 is becoming increasingly loaded with particulate matter. A limit line 60 may indicate the level of variation where regeneration of particulate filter 32 becomes desirable. When trend curve 58 reaches limit line 60, regeneration or cleaning of particulate filter 32 may be initiated by electronic control module 38, the user, and/or the service technician.

Figure 3B:
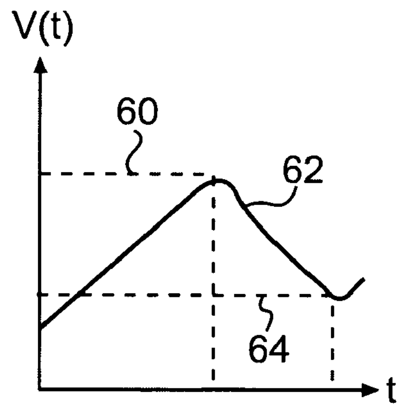
Figure 3C:
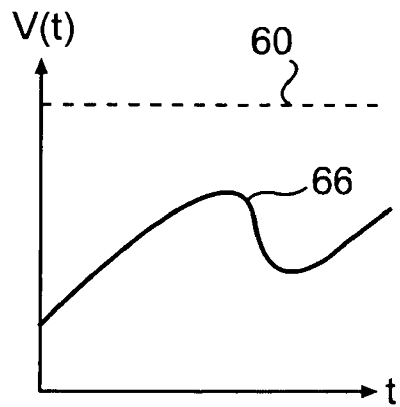

Trend curve 62 in FIG. 3B may be representative of the level of variation between the upstream and downstream sound waves before, during, and after regeneration of particulate filter 32. For example, trend curve 62 may include a rising portion and a falling portion. The rising portion may be similar to trend curve 58 in that both may indicate that particulate filter 32 is being loaded with particulate matter. The falling portion, on the other hand, may be indicative of a decrease in the level of variation over time that may occur as a result of regenerating particulate filter 32 to burn off, and thereby decrease, the amount of particulate matter in particulate filter 32. A lower limit line 64 may represent a level of variation where regeneration may cease. Thus, once the level of variation decreases to the limit line, regeneration device 34 may shut off, and particulate filter 32 may once again begin loading. In contrast, trend curve 66 in FIG. 3C shows an example of a curve that may be generated when particulate filter 32 is damaged. In trend curve 66, rising portions may be typical of the level of variation over time during loading of particulate filter 32. A sharply falling portion between the rising portions may indicate that the level of variation decreased over a short interval of time. This relatively sharp decrease may be the result of damage to particulate filter 32, such as, for example, formation of a gap or hole in particulate filter 32 that may allow sound waves to travel from transmitter 44 to receiver 48 without being filtered by filter element 40.

Electronic control module 38 may be calibrated so as to link a particular level or type of variation with a particular state of particulate filter 32, including, for example, clean, loading, loaded, and/or damaged. Associated with the particular level or type of variation may be a treatment or action that should be performed on particulate filter 32, such as, maintaining, cleaning, regenerating, or replacing, one or more parts of particulate filter 32.

It is contemplated that an analyzer (not shown) separate from electronic control module 38 may be used to perform the analysis on the upstream and downstream sound waves, and/or may trigger operation of particulate filter regeneration device 34. The analyzer may include, for example, one or more microprocessors and one or more memory components, similar to those used in electronic control module 38. Using an analyzer that is separate from electronic control module 38 may allow acoustic apparatus 36 to be portable, while providing acoustic apparatus 36 with the ability to operate independently from internal combustion engine 10 and/or electronic control module 38.

Electronic control module 38 may be operatively connected to particulate filter regeneration device 34 by a suitable electrical connection 50. Electronic control module 38 may send an electronic signal/pulse to particulate filter regeneration device 34 to initiate regeneration of particulate filter 32. Electronic control module 38 may determine the appropriate time to initiate regeneration based at least in part upon a time/maintenance schedule, historical performance data, and/or when the analysis of particulate filter 32 using acoustic apparatus 36 indicates that the amount of particulate matter trapped in particulate filter 32 has exceeded a predetermined value.

INDUSTRIAL APPLICABILITY

The disclosed acoustic apparatus may have applicability in diesel engine assemblies. Acoustic apparatus 36 may have particular applicability in monitoring the state of a particulate filter 32 of a diesel engine 10.

Figure 4:
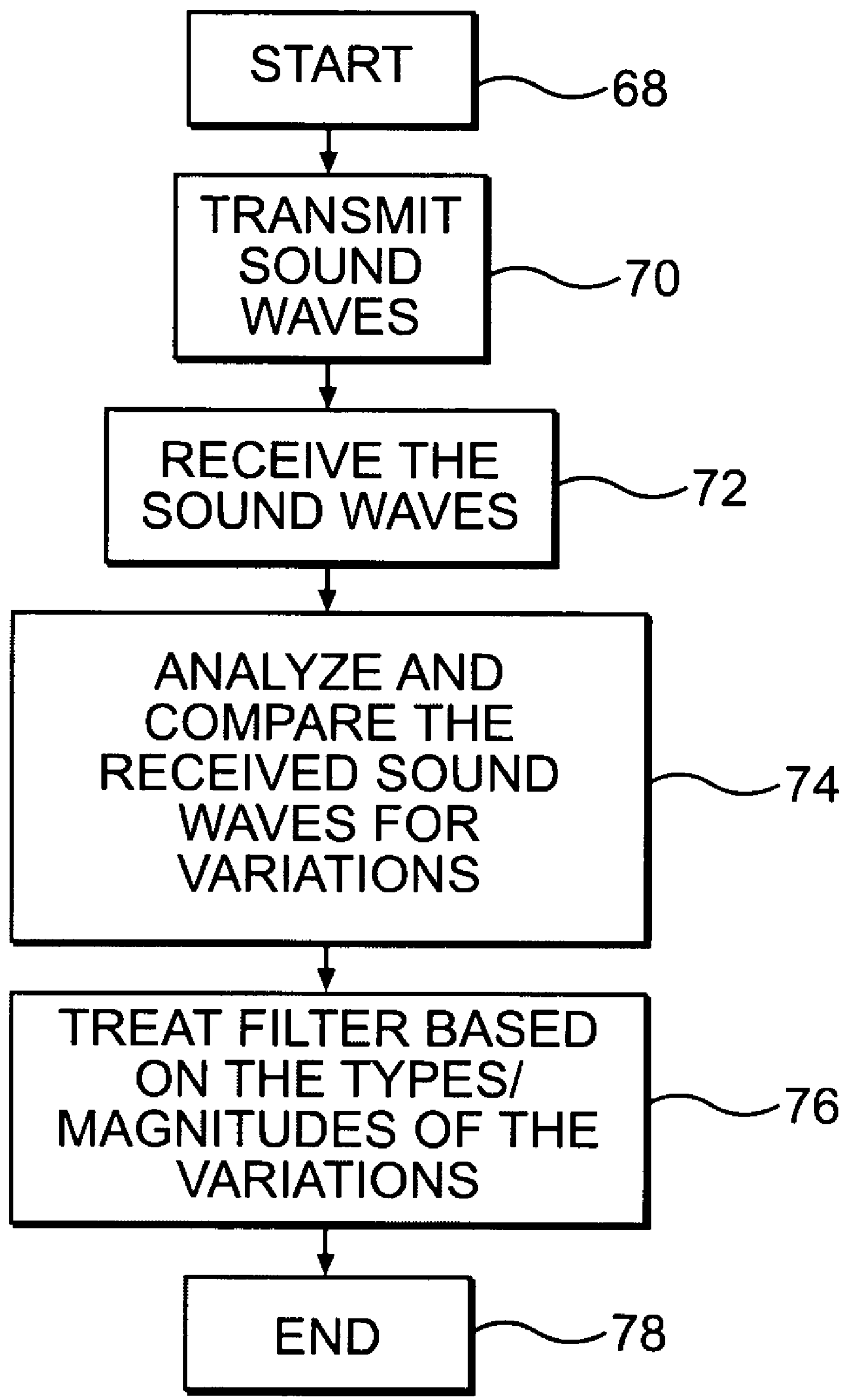
FIG. 4 is a flow diagram of a method for monitoring the state of a diesel particulate filter according to an exemplary embodiment of the present disclosure.

In the embodiment described in FIG. 4, acoustic apparatus 36 may include a transmitter 44, arranged on a first side of particulate filter 32, that starts (step 68) the monitoring process by transmitting sound waves, such as, for example, ultrasounds (step 70). The transmitted ultrasounds may be received (step 72) by a receiver 46, located on the same side of particulate filter 32 as transmitter 44, and a receiver 48, located on the opposite side of particulate filter 32. Receiver 46 may receive relatively unmodified ultrasounds that may be substantially identical to the ultrasounds transmitted by transmitter 44, and may convert these unmodified ultrasounds into electrical signals/pulses that may also be sent to an electronic control module 38. Receiver 48 may receive modified ultrasounds that have traveled through particulate filter 32, and may convert these modified ultrasounds into electrical signals/pulses that may also be sent to electronic control module 38. Electronic control module 38 may function as an analysis tool for analyzing (comparing and contrasting) the sound spectrum patterns and characteristics of the unmodified and modified ultrasounds (step 74) to determine the types and/or magnitudes of any variations between the unmodified and modified ultrasounds. Electronic control module 38 may maintain, clean, regenerate, or replace, particulate filter 32 (step 76) based at least in part on the types and/or magnitudes of the variations. This process may end (step 78) after treating particulate filter 32. Additionally or alternatively, the process may repeat continuously.

Using acoustic apparatus 36 to perform the analysis may be beneficial for many reasons. Acoustic apparatus 36 may produce sound waves that may allow acoustic apparatus 36 to perform relatively non-invasive analyses, meaning that neither particulate filter 32, exhaust line 14, nor their components need be removed to determine the state of particulate filter 32. This may help to minimize the amount of downtime, associated with scheduling and performing maintenance on a work machine (not shown) of which particulate filter 32 may be a part. The use of acoustical analysis may also allow monitoring of particulate filter 32 in real-time while internal combustion engine 10 is in operation. The sound waves, such as, for example, ultrasounds, transmitted/received by acoustic apparatus 36 may be relatively unaffected by variations in fuel characteristics, engine load, and/or engine back pressure, that may occur during actual operation of internal combustion engine 10. Thus, acoustic apparatus 36 may maintain its accuracy even in a dynamic engine environment. Additionally or alternatively, acoustic apparatus 36 may include a separate analyzer and/or power source, such that acoustic apparatus 36 may be portable, and capable of analyzing particulate filter 32 while internal combustion engine 10 is turned off. Because acoustic apparatus 36 may be removably attached to particulate filter 32 for testing, and may be subsequently removed and used on another particulate filter immediately thereafter, it may be particularly useful as an on-site diagnosis and/or preventative maintenance tool.

Acoustic apparatus 36 may also extend the working life of particulate filter 32, conserve fuel/energy, and help to maintain filtration capability, by controlling the timing, number, and/or duration of regenerations performed on particulate filter 32. For example, by using acoustic apparatus 36 to determine the state of particulate filter 32, damage to and/or clogging of particulate filter 32 may be directly measured without relying on back pressure sensor readings and similar devices that may not provide accurate indications of the actual state of particulate filter 32. Using the analysis performed by acoustic apparatus 36 as the basis for triggering regeneration can help to ensure that regeneration may take place when necessary, which may lead to increased filter efficiency and cleaner exhaust. Also, unnecessary regenerations may be avoided, which may help to preserve fuel/energy, while extending the working life of particulate filter 32.

It will be apparent to those skilled in the art that various modifications and variations can be made in the disclosed system and method without departing from the scope of the disclosure. Additionally, other embodiments of the disclosed system and method will be apparent to those skilled in the art from consideration of the specification. It is intended that the specification and examples be considered as exemplary only, with a true scope of the disclosure being indicated by the following claims and their equivalents.

What is claimed is:

1. A monitoring assembly for a filter, comprising:

a transmitter, arranged on a first side of the filter, configured to emit sound waves;

a first receiver, arranged on the first side of the filter, configured to receive the sound waves; and a second receiver, arranged on a second side of the filter, configured to receive the sound waves.

2. The assembly of claim 1, wherein the first side is an upstream side, from which engine exhaust enters the filter.

3. The assembly of claim 1, wherein the second side is a downstream side, from which engine exhaust exits the filter.

4. The assembly of claim 1, wherein the second receiver receives sound waves that have passed through the filter.

5. The assembly of claim 1, wherein the first and second receivers are configured to convert the sound waves into signals.

6. The assembly of claim 5, further including a control device, configured to receive the signals from the first and second receivers.

7. The assembly of claim 6, wherein the control device is configured to determine at least one value indicative of a variation between the first receiver signals and the second receiver signals.

8. The assembly of claim 7, wherein the control device is configured to activate a regeneration device to regenerate the filter if the magnitude of the value exceeds a predetermined level.

9. A method of monitoring a particulate filter, comprising:

transmitting sound waves from a first side of the filter with a transmitter;

receiving the sound waves on the first side of the filter with a first receiver;

receiving the sound waves on a second side of the filter with a second receiver; and determining at least one value indicative of a variation between the sound waves received on the first side and the sound waves received on the second side.

10. The method of claim 9, further including regenerating the filter if the magnitude of the at least one value is outside of a predetermined range.

11. The method of claim 9, further including replacing the filter if the magnitude of the at least one value is outside of a predetermined range.

12. The method of claim 9, wherein the sound waves are ultrasounds.

13. The method of claim 9, further including removable attaching at least one of the transmitter, first receiver, and second receiver, to the filter.

14. An engine assembly, comprising:

an engine having an exhaust line;

a particulate filter operatively coupled to the exhaust line; and an acoustic apparatus operatively coupled to at least one of the exhaust line and the particulate filter, the acoustic apparatus comprising:

a transmitter, arranged on a first side of the filter, configured to emit sound waves, a first receiver, arranged on the first side of the filter, configured to receive the sound waves, and a second receiver, arranged on a second side of the filter, configured to receive the sound waves.

15. The assembly of claim 14, wherein the first side is an upstream side, from which engine exhaust enters the filter, and the second side is a downstream side, from which engine exhaust exits the filter.

16. The assembly of claim 14, wherein the second receiver receives sound waves that have passed through the filter.

17. The assembly of claim 14, wherein the first and second receivers are configured to convert the sound waves into signals.

18. The assembly of claim 17, further including a control device, configured to receive the signals from the first and second receivers.

19. The assembly of claim 18, wherein the control device is configured to determine at least one value indicative of a variation between the first receiver signals and the second receiver signals.

20. The assembly of claim 19, wherein the control device is configured to activate a regeneration device to regenerate the filter if the magnitude of the value exceeds a predetermined level.

* * * * *

UNITED STATES PATENT AND TRADEMARK OFFICE

CERTIFICATE OF CORRECTION

PATENT NO. : 7,395,710 B2
APPLICATION NO. : 11/362863
DATED : July 8, 2008
INVENTOR(S) : Mohamed Daoud It is certified that error appears in the above-identified patent and that said Letters Patent is hereby corrected as shown below:

Column 3, line 66, delete "bum" and insert -- burn --.

Signed and Sealed this

Twenty-fourth Day of February, 2009

JOHN DOLL
*Acting Director of the United States Patent and Trademark Office*